United States Patent [19]
Beeler et al.

[11] Patent Number: 5,573,935
[45] Date of Patent: Nov. 12, 1996

[54] PROTEIN TYROSINE KINASE A6

[75] Inventors: John F. Beeler, Bethesda; William Larochelle, Gaithersburg, both of Md.; Stuart A. Aaronson, Great Falls, Va.

[73] Assignee: The United States of America as represented by the Department of Health and Human Services, Washington, D.C.

[21] Appl. No.: 184,252

[22] Filed: Jan. 18, 1994

[51] Int. Cl.$^6$ .................. C12N 9/12; C12N 15/54; C12N 15/70; C12N 15/74

[52] U.S. Cl. .................. 435/194; 435/69.8; 435/252.33; 435/252.3; 435/320.1; 536/23.2; 536/23.5; 930/240

[58] Field of Search .................. 435/69.8, 194, 435/252.3, 252.33, 320.1; 536/23.2, 23.5; 930/240

[56] References Cited

U.S. PATENT DOCUMENTS 5,283,354  2/1994  Lemischka .................. 435/69.1

OTHER PUBLICATIONS

Stuart A. Aaronson, "Growth Factors and Cancer", *Science*, 254: 1146–1153, 1991.

Ben–David, et al. "A Mammalian Protein Kinase With Potential For Serine/Threonine And Tyrosine Phosphorylation Is Related To Cell Cycle Regulators", *Embo J.*, 10: 317–325, 1991.

Hanks, et al., "The Protein Kinase Family: Conserved Features And Deduced Phylogeny Of The Catalytic Domains", *Science*, 241: 42–48, 1988.

Haring, et al., "Phosphorylation And Dephosphorylation Of The Insulin Receptor: Evidence Against An Intrinsic Phosphatase Activity", *Biochemistry* 23: 3298–3306, 1984.

Hunter, et al., "Protein–Tyrosine Kinases", *Annu. Rev. Biochem.* 54: 897–930, 1985.

Ishibashi, et al., "Expression Cloning Of A Human Dual-Specificity Phosphatase", *Proc. Natl. Acad. Sci. USA* 89: 12170–12174, 1992.

Klumpp, et al., "Nucleotide Sequence of aceK, The Gene Encoding Isocitrate Dehydrogenase Kinase/Phosphatase" *J. Bacteriol.* 170: 2763–2769, 1988.

Letwin, et al., "Novel Protein–Tyrosine Kinase cDNAs Related To *fps/fes* And *eph* Cloned Using Anti–Phosphotyrosine Antibody", *Oncogene* 3: 621–627, 1988.

Lindberg, et al., "Dual–Specificity Protein Kinases: Will Any Hydroxyl Do?", *Trends Biochem. Sci.* 17: 114–119, 1992.

Lindberg, et al., "Identification of cDNA Clones That Code for Protein–Tyrosine Kinases By Screening Expression Libraries With Antibodies Against Phosphotyrosine", *Oncogene* 3: 629–633, 1988.

Kraus, et al., "Detection And Isolation Of Novel Protein–Tyrosine Kinase Genes Employing Reduced Stringency Hybridization" *Methods Enzymol.* 200: 546–556, 1991.

Maru, et al., "The BCR Gene Encodes A Novel Serine/Threonine Kinase Activity Within A Single Exon" *Cell*, 67: 459–468, 1991.

Wilks, "Cloning Members of Protein–Tyrosine Kinase Family Using Polymerase Chain Reaction", *Methods Enzymol.* 200: 533–546, 1991.

Wu, et al. "The Hepatitis B Virus–Encoded Transcriptional *Trans*–Activator hbx Appears To Be A Novel Protein Serine/Threonine Kinase", *Cell*, 63: 687–695, 1990.

Yonezawa, et al., "A Short Sequence Responsible For Both Phosphoinositide Binding And Actin Binding Activities of Cofilin", *J. Biol. Chem.* 266: 17218–17221, 1991.

Guan, et al., "Eukaryotic Proteins Expressed In *Escherichia Coli*: An Improved Thrombin Cleavage And Purification Procedure Of Fusion Proteins With Glutathione S–Transferase", *Anal. Biochem.* 192: 262–267, 1991.

Kornbluth, et al. "Novel Tyrosine Kinase Identified By Phosphotyrosine Antibody Screening Of cDNA Libraries", *Mol. Cell. Biol.* 8: 5541–5544, 1988.

Icely, et al. "Tik, A Novel Serine/Threonine Kinase, Is Recognized By Antibodies Directed Against Phosphotyrosine", *J. Biol. Chem.* 266: 16073–16077, 1991.

Beeler, et al. (1994) "Prokaryotic Expression Cloning Of A Novel Human Tyrosine Kinase", *Molecular And Cellular Biology* 14(2):982–988.

Schatz et al, "The V(D)J Recombination Activating Gene, RAG–1", *Cell* 59: 1035–1048.

Sambrook et al, *Molecular Cloning*, pp. 14.14–14.15, (Cold Spring Harbor Laboratory Press 1989).

Reeck et al " 'Homology' in Proteins and Nucleic Acids . . ." *Cell* 50:667.

Sambrook et al, p. 16.3 in *Molecular Cloning*, 2nd Ed. (1989).

Adams et al "Rapid cDNA sequencing . . ." *Nature Genetics* 4(4):373–380 (Aug. 1993).

Primary Examiner—Stephen G. Walsh
Attorney, Agent, or Firm—Knobbe, Martens, Olson & Bear

[57] ABSTRACT

A novel protein tyrosine kinase (A6) exhibiting no significant similarity to any known kinase. This protein in widely expressed throughout the body and is present in a variety of vertebrates. The cDNA was expressed in bacteria as a fusion protein which was both autophosphorylated and exhibited kinase activity toward exogenous substrates. Potential uses of this invention include immunodiagnostics and antiproliferative therapeutics.

10 Claims, 1 Drawing Sheet

```
                                                                              129
COFILIN    100  F I F W A P E S A P L K S K M I Y A S S K D A I K K K F T G
ACTOPHORIN  82  F I L W A P D S A P I K S K M M Y T S S T K D S I K K L V G   111
ADF         87  F I S W S P D T S R V R S K M L Y A S S T K D R F K R E L D G 116
A6          85  F I A W S P D H S H V R Q K M L Y A A T R A T L K K E F G G   114
```

Fig. 1

PROTEIN TYROSINE KINASE A6

FIELD OF THE INVENTION

This invention relates to protein tyrosine kinases. More specifically, it relates to the cloning of a human gene encoding a novel protein tyrosine kinase unrelated to any previously identified protein kinase.

BACKGROUND OF THE INVENTION

Protein phosphorylation has been implicated in a number of important physiologic events ranging from normal cell growth and differentiation to malignant transformation. Phosphorylation is mediated by a superfamily of enzymes known as protein kinases. In eukaryotic cells, these enzymes phosphorylate hydroxyl groups of serine (ser), threonine (thr) and tyrosine (tyr) residues by transferring the λ phosphate from ATP using a magnesium or manganese ion cofactor. Tyrosine kinases, unlike ser/thr kinases, prefer manganese ion over magnesium ion. Although the vast majority of kinases are specific to either tyr or ser/thr, several recently-described kinases can phosphorylate all three residues (Ben-David et al., (1991) *EMBO J.*, 10: 317–325; Howell et al., (1991) *Mol. Cell. Biol.*, 11: 568–572). These proteins are called "dual specificity protein kinases" (Lindberg et al., (1992) *Trends Biochem. Sci.*, 17: 114–119).

Tyrosine phosphorylation is an early signal transduction event which occurs after the binding of growth factors, hormones or cytokines to cell surface receptors and is a mechanism by which a number of oncogene products exert their proliferation-inducing effects (Aaronson, (1991) *Science*, 254: 1146–1153; Hanks et al., (1988) *Science*, 241: 42–52; Hunter and Cooper, (1985) *Annu. Rev. Biochem.*, 54: 897–930). Oncogenes are mutated forms of normal genes (proto-oncogenes) which have been picked up by retroviruses. Most proto-oncogenes encode proteins mediating events by which growth factors stimulate normal cell division (Cantley et al., (1991) *Cell*, 64: 281–302). For example, the v-src and v-abl genes encode transforming tyrosine kinases from Rous sarcoma virus and Abelson murine leukemia virus, respectively, which are oncogenic counterparts of the corresponding normal cellular genes. These kinases may be classified as either receptor (v-erb B, v-neu) or nonreceptor (v-src, v-abl) tyrosine kinases.

Changes in tyrosine phosphorylation are believed to be responsible for initiating reaction cascades leading to the covalent modification of proteins. In some instances, these other proteins are kinases. Many of these proteins, including $p34^{cdc2}$, and the platelet derived growth factor receptor, are either protein kinases or are regulated by their phosphorylation state. Since several protein kinases, including $p34^{cdc2}$, regulate entry and progression through the cell cycle, they thus represent important control points in cell growth.

To elucidate the mechanisms involved in the control of cell proliferation, additional novel kinases have been identified by either low stringency hybridization and polymerase chain reaction using primers corresponding to conserved kinase regions (Kraus and Aaronson, (1991) *Methods Enzymol.*, 200: 546–556; Wilks, (1991) *Methods Enzymol., 200: 543–546*) or by expression cloning (Lindberg et al., (1988) *Oncogene*, 3: 629–633). Enzymatically active tyrosine kinases undergo autophosphorylation on their own tyrosine residues, allowing their detection by antibodies against phosphotyrosine (pTyr). Since bacteria lack protein tyrosine kinases (PTKs), antibodies to pTyr have been particularly useful in the identification and characterization of several novel kinases isolated from bacterial expression systems (Kornbluth et al., (1988) *Mol. Cell Biol.*, 8: 5541–5544; Letwin et al., (1988) *Oncogene*, 3: 621–627). Most recently, two novel protein kinases called TIK and TTK have been described (Icely et al., (1991) *J. Biol. Chem.*, 266: 16073–16077; Mills et al., (1992) *J. Biol. Chem.*, 267: 16000–16006). TIK is a ser/thr kinase containing consensus ser/thr kinase catalytic residues while TTK is predominantly a ser/thr kinase with a low level of tyrosine phosphorylation activity and is associated with cell proliferation.

BRIEF DESCRIPTION OF THE FIGURE

FIG. 1 shows the sequence alignment of amino acids 85–114 of the A6 sequence shown in SEQ. ID NO: 2 with homologous regions in cofilin, (SEQ. ID NO: 5) actophorin (SEQ. ID NO: 6) and actin depolymerizing factor (ADF). (SEQ ID NO: 7) Conserved amino acids are boxed.

SUMMARY OF THE INVENTION

One embodiment of the present invention is an isolated polynucleotide encoding the human A6 protein tyrosine kinase. Preferably, this polynucleotide has the sequence corresponding to the coding region of SEQ ID NO: 1. In another aspect of this preferred embodiment, there is provided an isolated nucleotide sequence having homology to at least 18 contiguous nucleotides of this polynucleotide. Another aspect of the invention provides non-human species variations of the isolated tyrosine kinase.

According to another embodiment of the invention, there is provided a recombinant construct comprising the coding region of SEQ ID NO: 1 operably linked to a heterologous promoter in an expression vector. Advantageously, this recombinant construct is expressed in cells. Preferably, these cells are prokaryotic; most preferably, they are *E. coli* Y1089 cells. According to another aspect of this preferred embodiment, the expression vector is λpCEV1acz which contains the β-galactosidase promoter and gene sequence. Preferably, the sequence corresponding to SEQ ID NO: 1 is adjacent to the β-galactosidase gene, and upon expression the protein encoded by SEQ ID NO: 1 and β-galactosidase form a fusion protein.

In accordance with another aspect of the invention, there is provided a completely new human protein tyrosine kinase having a molecular weight of about 40,000 daltons, designated A6, in isolated form. Preferably, this kinase has the amino acid sequence corresponding to SEQ ID NO: 2. In another aspect of this preferred embodiment, there are provided non-human species variations of the A6 kinase.

Still another embodiment of the present invention is isolated antibodies against the A6 protein tyrosine kinase. Preferably, these isolated antibodies are monoclonal; most preferably, they are either BF2 or DA6. According to another aspect of this preferred embodiment, the antibodies are polyclonal.

DETAILED DESCRIPTION OF THE INVENTION

The present invention discloses the prokaryotic expression cloning and in vitro characterization of a novel human protein tyrosine kinase. This protein kinase is highly divergent from previously described members of this important class of regulatory molecules. Nucleotide sequence analysis revealed that the predicted protein lacked consensus amino acid sequences commonly found in protein kinases. This kinase may be important in the regulation of cellular growth control pathways.

The human A6 gene sequence, fragments thereof, vectors containing this sequence or fragments thereof, cells transfected with this sequence or fragments thereof and protein purified from these cells are useful for studying the cellular distribution and expression of the A6 protein kinase. The expressed recombinant A6 protein is useful as a reagent for converting Tyr to pTyr. One of ordinary skill in the art who desires a particular tyrosine-phosphorylated protein can combine the expressed protein or β-galactosidase fusion protein in a reaction container with ATP, magnesium or manganese ion and the protein to be phosphorylated, as shown in Examples 3 and 4. Fragments of the A6 protein kinase gene consisting of at least 18 consecutive nucleotides unique to A6 are useful as polymerase chain reaction (PCR) probes for isolating other members of this new kinase family as well as the corresponding receptor gene from other species (See Example 10). These oligonucleotides are also useful for in situ hybridization and for probing Northern blots of RNA isolated from various tissues by well known methods to determine the A6 protein kinase distribution.

In addition, DNA sequences of 18 nucleotides correspond to six amino acids. Those of ordinary skill in the art will appreciate that a six amino acid peptide, when coupled to an immunogenic carrier protein such as keyhole limpet hemocyanin (KLH) or ovalbumin, can be utilized as an immunogen to raise antibodies against A6 kinase epitopes. Alternatively, the A6 kinase cDNA or fragments thereof can be expressed and the resulting polypeptide recovered and used as an immunogen. Antibodies against the A6 protein will allow immuno-histochemical localization of the protein in cells, tissues and body fluids.

The use of a number of prokaryotic expression vectors in addition to λpCevlacz is also within the scope of the present invention. Although the A6 kinase was expressed as a lacz fusion protein, the expression of the protein itself by minor technical modifications known to one of ordinary skill in the art, is also envisioned. In addition, the use of eukaryotic expression vectors and transfection of eukaryotic cells is also contemplated. However, eukaryotic cells possess endogenous kinase activity, so mock-transfected cell protein kinase activity must be subtracted from transfected cell protein kinase activity to determine true A6 kinase activity.

One of ordinary skill in the art will appreciate that the A6 gene sequence can be rapidly incorporated into almost any desired vector. In the present invention, the most preferable expression vectors are prokaryotic, although the use of yeast and viral, particularly baculoviral, expression vectors is also within the scope of the present invention, as is the production of the A6 kinase or fragments thereof in these cell types.

Antibodies generated against the A6 protein tyrosine kinase will be useful in the production of diagnostic kits for determining the level of the A6 kinase in both normal and neoplastic tissue to correlate its activity with cell proliferation. Antibodies against A6 will also be useful in cellular localization of the A6 kinase by immunocytochemistry. Further, these antibodies can be used for affinity chromatography to isolate large quantities of the expressed protein.

Inhibitors of the A6 kinase will be useful in controlling A6-mediated cell growth. Any of the known tyrosine kinase inhibitors may exhibit particular specificity toward the A6 kinase as described in Example 9. With the gene sequence determined, mutations can now be introduced in order to study structure-function relationships as they relate to ATP and pTyr binding and to effector system coupling. This information will be useful in the design of inhibitors able to specifically block A6 kinase activity which may inhibit aberrant cellular growth processes including neoplastic growth, atherosclerosis and psoriasis. Identification and characterization of this novel protein kinase will help elucidate the processes controlling both normal and aberrant cell growth.

The recombinantly expressed kinase will also be useful in screening new kinase inhibitors both in vitro and in vivo. The bacterial system is especially well-suited for this purpose since the lack of endogenous protein tyrosine kinases will greatly decrease background binding of the potential inhibitors to endogenous proteins. Any background binding may be attributed to inhibition of endogenous ser/thr kinases, although this background binding is expected to be very low since bacteria contain low levels of these proteins.

To identify novel tyrosine kinases unrelated to previously identified members of the PTK superfamily, a human lung fibroblast cDNA library was screened with a monoclonal antibody to pTyr as described in the following example.

EXAMPLE 1 cDNA library construction and screening

Human lung fibroblast M426 cells were developed in the laboratory of Stuart Aaronson, National Cancer Institute, National Institutes of Health, Bethesda, Md. An expression library was constructed by well known methods using oligo (dT)-primed M426 human lung fibroblast cDNA packaged into the prokaryotic expression vector λpCEVlacz which contains the β-galactosidase (lacz) promoter and gene sequence (Ishibashi et al., (1992) Proc. Natl. Acad. Sci. U.S.A., 89: 12170–12174). For library screening, the bacterial strain Y1090 was infected with phage ($2\times10^4$ per 150 mm plate) and plated on agar plates containing 50 µg/ml ampicillin. The plates were incubated for 4 hours at 37° C., overlayed with nitrocellulose filters pretreated with 10 mM isopropyl-1-thio-β-D-galactopyranoside (IPTG) and incubated for 6 hours at 37° C. Filters were rinsed in TTBS (25 mM Tris-HCl, pH 7.5, 150 mM NaCl, 0.05% Tween-20) and nonspecific binding sites were blocked with 3% nonfat dry milk in TTBS for 1 hour at room temperature. The filters were probed with the mouse monoclonal anti-pTyr antibody 4G10 (Upstate Biotechnology, Inc., Lake Placid, N.Y.) overnight, washed twice with TTBS and positive clones were detected with [$^{125}$I] labeled protein A for 1 hour. Filters were washed four times with TTBS, air-dried and exposed to Kodak XAR film (Eastman Kodak, Rochester, N.Y.) overnight at −70° C. Positive plaques were isolated and subjected to secondary and tertiary screenings, resulting in pure plaques.

The cDNA inserts from plaque-purified clones were sequenced using Sequenase™ (United States Biochemical, Cleveland, Ohio). The majority of the positive clones were identified as the tyrosine kinases src or fyn based on the molecular weights of the deduced encoded proteins. However, one clone, designated A6, contained a 3 kilobase insert designated as SEQ ID NO: 1 whose deduced amino acid sequence exhibited little or no sequence similarity to any known protein.

Nucleotide and predicted amino acid sequence of A6

The open reading frame (ORF) of SEQ ID NO: 1 encoding the A6 kinase consisted of 1050 base pairs starting with an initiating methionine codon at position 61 and ending with a TAA termination codon at nucleotide 1110. The open reading frame was flanked by 5' and 3' untranslated regions consisting of 60 and 1890 nucleotides, respectively, with a putative polyadenylation signal (AATAAA) at position 2953. Translation of the ORF resulted in a 350 amino acid protein with a calculated molecular weight of 40,285 daltons.

To search for clones containing additional 5' untranslated sequence, the 3 kilobase A6 fragment was used to screen the M426 cDNA library. Analysis of nine additional clones indicated the absence of any additional 5' untranslated sequence.

Computer analysis of the deduced A6 protein sequence

Computer analysis using the Prosite program (Bairoch, (1992) *Nucleic Acids Res.*, 20:2013–2018) revealed that the predicted A6 amino acid sequence lacked an amino terminal secretory signal sequence and a membrane spanning domain. A consensus N-myristoylation site (GEDRKHP-FYW-XX-STAGCNP) (SEQ. ID. NO. 8) was found at gly6. N-myristoylation is a post-translational modification of a number of oncogenic tyrosine kinases which allows anchoring to the cell membrane via the myristate lipid moiety. Several potential protein kinase C phosphorylation sites (S/T-X-R/K) were found at thru$_{107}$, thru$_{124}$, ser$_{233}$, ser$_{265}$ and ser$_{274}$. Two consensus tyrosine kinase phosphorylation sites were found at tyr$_{236}$ and tyr$_{249}$. The A6 protein was analyzed for similarity to existing sequences using the National Center for Biotechnology Information (NCBI) BLAST network service (Altschul et al., (1990) *J. Mol. Biol.*, 215: 403–410). Searches of NCBI databases (SWISS-PROT 25.0, PIR 36.0 and GenPept-GenBank 76.0) as well as the Protein Kinase Catalytic Domain Data Base (Hanks and Quinn, (1991) *Methods Enzymol.*, 200: 38–62) indicated that A6 showed no significant similarity to any known protein.

The protein kinase family, which includes more than 100 members of eukaryotic origin, all have a discrete catalytic domain that can be divided into twelve different subdomains (Hanks and Quinn, supra.). The conserved features within these subdomains help to define a consensus sequence for protein kinases. The A6 sequence did not exhibit any of the sequence motifs commonly conserved among protein kinases as judged by using the pattern and matching programs of the University of Wisconsin Genetics Computer Group's Motifs, ProfileScan and Profile Gap computer programs (Carrera et al., (1993) *Proc. Natl. Acad. Sci. U.S.A.*, 90: 442–446).

Although proteins exhibiting kinase activity but having little or no similarity to the catalytic domains of protein kinases have been described, computer analysis of the deduced A6 sequence failed to reveal significant similarity with the following "atypical" kinases: BCR (Maru and Witte, (1991) *Cell*, 67: 459–468), the hepatitis B virus transactivator protein HBx (Wu et al., (1990) *Cell*, 63: 687–695) and aceK, an isocitrate dehydrogenase kinase/phosphatase specific for ser/thr residues from *E. coli* (Klumpp et al., (1988) *J. Bacteriol.*, 170: 2763–2769). For further comparison, pairwise alignments between the A6 sequence, representatives of the major protein kinase subfamilies, and the "atypical" kinases BCR and HBx, were generated using the FASTA program (Pearson and Lipman, (1988) *Proc. Natl. Acad. Sci. U.S.A.*, 85: 2444–2448). The RDF2 program was used to judge the statistical significance of the alignments (Pearson and Lipman, supra). Alignment scores generated by the FASTA program are shown in Table 1; scores of 80 and higher reflect significant similarity. Although no significant similarities were observed between the "atypical" kinases and any other protein kinase, relationships between various subfamilies were readily observed. The A6 sequence contained a potential catalytic subdomain I/II motif (Hanks et al., (1988) *Science*, 241: 42–48) with residues 113–123 representing the glycine-rich region characteristic of a nucleotide binding domain followed by a downstream lysine (lys$_{135}$) which is a critical residue for proper phosphotransferase activity (Ben-David et al., (1991) *EMBO J.*, 10: 379 317–325). However, similarity to other subdomains was not observed. Thus, the A6 gene encodes a unique "atypical" kinase.

To determine whether a kinase activity was associated with the protein encoded by the A6 gene, the protein was expressed in bacteria and the recombinant protein analyzed as described below.

TABLE 1

Comparison of the predicted A6 amino acid sequence to those of the catalytic domains of representative protein kinases

| | Atypical | | | Dual-Specificity | | | | | Tyrosine | | |
|---|---|---|---|---|---|---|---|---|---|---|---|
| | A6 | BCR | HBX | CLK | DPYK1 | MCK1 | MIK1 | MKK1A | C-SRC | MET | PDGFR-α |
| A6 | 1730 | | | | | | | | | | |
| BCR | 49 | 1233 | | | | | | | | | |
| HBx | 39 | 30 | 833 | | | | | | | | |
| CLK | 29 | 32 | 34 | 1736 | | | | | | | |
| DPYK1 | 27 | 23 | 31 | 109 | 1439 | | | | | | |
| MCK1 | 33 | 44 | 37 | 176 | 85 | 1621 | | | | | |
| MIK1 | 28 | 27 | 32 | 101 | 113 | 164 | 1376 | | | | |
| MKK1A | 30 | 54 | 31 | 109 | 107 | 195 | 207 | 1147 | | | |
| C-SRC | 34 | 28 | 27 | 98 | 200 | 140 | 138 | 171 | 1330 | | |
| MET | 29 | 33 | 34 | 47 | 113 | 111 | 138 | 171 | 447 | 1376 | |
| PDGFR-α | 41 | 32 | 36 | 82 | 160 | 167 | 97 | 137 | 395 | 414 | 1809 |
| C-MOS | 55 | 32 | 37 | 77 | 119 | 146 | 118 | 146 | 171 | 183 | 155 |
| PKC-γ | 44 | 35 | 30 | 107 | 105 | 191 | 179 | 205 | 222 | 177 | 152 |
| RKS1-C | 69 | 29 | 33 | 132 | 130 | 195 | 36 | 183 | 153 | 126 | 152 |

The A6 sequence was compared to known protein kinases using the FASTA program. The values represent the optimized alignment scores and values of 80 or higher indicate significant similarity. Designations for representative protein kinase catalytic domain sequences were taken from the protein kinase data base of Hanks and Quinn (8) except for BCR (21) and HBx (27).

EXAMPLE 2

Bacterial expression of β-gal-A6 fusion protein

The E. coli strain Y1089 was grown to log phase ($OD_{600}$=0.4) in NZY media and infected with the λpCEVlacz vector from Example 1 containing the A6 gene at a multiplicity of infection of 10:1 (phage:cells). Cells were grown in the presence of 100 μM IPTG for 2 hours at 37° C. to induce expression of the β-galactosidase-A6 fusion protein. For analysis of bacterial lysates, 1 ml aliquots of lysed cells were centrifuged to pellet the membranes and cell debris and resuspended in 100 μl 2×SDS sample buffer (0.125 M Tris-HCl, pH 6.8, 4% SDS, 20% glycerol, 0.1M dithiothreitol, 0.2% bromphenol blue). Samples (20–40 μl each) were analyzed by sodium dodecyl sulfate-polyacrylamide gel electrophoresis (SDS-PAGE). For immunoprecipitations, cells were resuspended in Nonidet™ P-40 (NP-40) lysis buffer (50 mM Tris-HCl, pH 8.0, 150 mM NaCl, 1 mM EDTA, 1% NP-40, 100 mM phenylmethylsulfonylfluoride (PMSF), 10 μg/ml pepstatin) and lysed by sonication. Lysates were clarified by centrifugation at 14,000×g for 10 minutes.

SDS-PAGE analysis of bacterial cell lysates infected with λpCEVlacz-A6 revealed the presence of a 150 kDa protein induced by IPTG. Since the λpCEVlacz expression vector alone encoded only the 110 kDa β-gal fusion protein, the deduced molecular weight of the A6 expression product itself was approximately 40 kDa, in good agreement with the calculated molecular weight based on the deduced amino acid sequence (Example 1). To confirm that the 150 kDa protein was a β-gal fusion product, bacterial lysates were analyzed by immunoblotting using either a mouse monoclonal anti-β-galactosidase antibody (Promega, Madison, Wis.) or anti-pTyr. Bands were visualized using [$^{125}$I] protein A. The λpCEVlacz-A6 fusion product was detected as a predominant immunoreactive species of approximately 150 kDa, consistent with the size of the IPTG inducible protein.

EXAMPLE 3

Determination of β-gal-A6 fusion protein kinase activity

To characterize the protein kinase activity of the β-gal-A6 fusion protein, lysates from bacteria expressing β-gal-A6 or β-gal alone were analyzed by immunoblotting with anti-pTyr. A predominant 150 kDa species was detected in β-gal-A6 lysates, consistent with the signal of the β-gal-A6 fusion protein mentioned in Example 2. A number of additional anti-pTyr reactive proteins were also detected in the β-gal-A6 lysates. Although lower molecular weight species may represent degradation products of the fusion protein, immunoreactive proteins greater than 150 kDa were also observed. This indicated that the fusion protein phosphorylated endogenous bacterial proteins. Immunoreactivity of anti-pTyr with the fusion product, as well as with the other proteins, was completely inhibited by pretreatment of cell lysates with alkaline phosphatase which removes phosphate groups, or by preincubation of the antipTyr with the competitive inhibitor phosphotyrosine (1 mM), but not with 1 mM phosphoserine or phosphothreonine. These results strongly suggested that β-gal-A6 was tyrosine phosphorylated in bacteria.

To establish that the A6 protein was a tyrosine kinase, lysates of bacterial cells expressing β-gal-A6 or β-gal alone were immunoprecipitated with anti-β-gal and the immune complexes analyzed by an in vitro kinase assay as described in the following example.

EXAMPLE 4

In vitro kinase assay of β-gal-A6 immunoprecipitates

Cleared lysates were immunoprecipitated with either anti-β-gal or anti-pTyr and washed twice with 1 ml NP-40 lysis buffer and twice with 1 ml kinase reaction buffer (50 mM HEPES, pH 7.4, 1% NP-40). Immunoprecipitates were resuspended in kinase reaction buffer containing 10 mM $MnCl_2$ followed by addition of 20 μCi [γ-$^{32}$P] ATP for 20 minutes at room temperature. Myelin basic protein (MBP) and poly(glu-tyr, 4:1) (Sigma, St. Louis, Mo.) were included as exogenous protein kinase substrates where indicated. Reactions were terminated by the addition of 2×SDS sample buffer and $^{32}$P labeled proteins were resolved by SDS-PAGE. In some cases proteins were transferred to Immobilon-P membranes (Millipore, Beverly, Mass.). Protein bands were visualized by autoradiography.

SDS-PAGE analysis of immunoprecipitates from β-gal-A6 lysates revealed a $^{32}$P-labeled 150 kDa protein, consistent with the predicted molecular weight of the β-gal fusion protein. In contrast, no $^{32}$P-labeled proteins were detected in immunoprecipitates from lysates expressing β-gal alone. These results indicated an in vitro kinase activity associated with the A6 protein. The ability of the β-gal-A6 fusion protein to phosphorylate MBP and poly (glu-tyr), known in vitro substrates of a variety of tyrosine kinases, was also examined. The β-gal-A6 fusion protein was able to phosphorylate both substrates.

To identify the residues phosphorylated in the A6 protein itself and in the exogenous substrates, phosphoamino acid analysis was performed as described below.

EXAMPLE 5

Phosphoamino acid analysis

Phosphoamino acid analysis was performed as previously described (Haring et al., (1984) Biochemistry, 23: 3298–3306). Briefly, bands of interest were hydrolyzed from Immobilon-P membranes by incubation with 6M HCl for 2 hours at 110° C. Sample volumes were adjusted to 1 ml with water and the HCl was removed under vacuum. Hydrolysates were washed with water, centrifuged under vacuum, resuspended in a mixture of pSer, pThr, and pTyr (1 mg/ml each), and analyzed by thin layer electrophoresis. Two dimensional analysis was performed at pH 1.9 for 60 min at 1 kV (first dimension) and at pH 3.5 for 50 min at 1 kV (second dimension). One dimensional analysis was performed at pH 3.5 for 60 min. Phosphoamino acid standards were visualized by staining with ninhydrin.

The results indicated that the A6 kinase was phosphorylated on both tyrosine and serine residues. However, the exogenous kinase substrates MBP and poly (glu-tyr) were phosphorylated exclusively on tyrosine.

To examine the distribution of A6 gene expression, we performed Northern blot analysis on RNA isolated from a variety of human tissue, as described in the following example.

EXAMPLE 6

Northern analysis of A6 RNA

M426 cell monolayers in 100 mm culture dishes were washed in PBS, lysed in the presence of the RNase inhibitor RNAzol (TelTest, Inc., Friendswood, Tex.) and extracted with chloroform. Human tissues were pulverized in liquid nitrogen and homogenized in the presence of RNAzol with a polytron. Chloroform (0.2 ml per 2 ml homogenate) was added and the samples were shaken vigorously for 15 seconds and left on ice for 5 minutes. The suspension was centrifuged at 12,000×g at 4° C. for 15 minutes. The aqueous phase containing the RNA was transferred to a fresh tube and the RNA was precipitated with an equal volume of isopropanol for 15 min at 4° C. Samples were centrifuged for 15 min at 12,000×g at 4° C. The RNA pellet was washed with 75% ethanol, dried briefly under vacuum and dissolved in 10 mM Tris-HCl, pH 7.0, 1 mM EDTA. RNA concentrations were determined by absorbance at 260 nm.

Twenty μg total RNA was analyzed by electrophoresis on 1% agarose gels containing 2.2M formaldehyde and transferred to Nytran (Schleicher and Schuell, Keene, N.H.) nylon membranes. After crosslinking of RNA to the membrane, filters were prehybridized for 2 hours at 42° C. in Hybrisol (50% formamide, 10% dextran sulfate, 1% SDS, 6×standard saline citrate (SSC) and blocking agents; Oncor, Gaithersburg, Md.). Filters were then hybridized for 20 hours in the same solution containing the $^{32}$P-labeled 3 kilobase SalI fragment A6 DNA probe. Filters were washed twice for 30 min each at room temperature in 2×SSC, 1% SDS, then twice at 50° C. in 0.1×SSC, 1% SDS and exposed to Kodak XAR film.

Under stringent hybridization conditions, the A6 cDNA probe revealed a single transcript of approximately 3.4 kilobases in various tissues consistent with its size in M426 cells. The A6 message was expressed at high levels in the colon, testes, uterus, ovary, prostate and lung. Lower levels were found in the brain, bladder and heart with no detectable transcript present in the liver. This distribution indicates the presence of high levels of the A6 kinase in tissues exhibiting a large amount of cell shedding and reproliferation, while lower levels are present in more static tissues. In addition, the A6 cDNA probe detected related genomic DNA fragments in other vertebrates including mice, amphibians and fish. The A6 gene thus appears to be highly conserved in vertebrate evolution.

EXAMPLE 7

Production of polyclonal antibodies against human A6 kinase

Synthetic peptides corresponding to the N- and C-terminal regions of the A6 kinase were synthesized on an Applied Biosystems Model 430A peptide synthesizer. The N-terminal and C-terminal peptides corresponded to amino acids 1–17 and 325–342 of SEQ ID NO: 2, respectively. Peptides were conjugated to the immunogenic carrier protein thyroglobulin as follows: 2 mg peptide was mixed with 24 mg thyroglobulin in 2 ml 0.1M sodium phosphate, pH 7.5 and then incubated with 1 ml 20 mM glutaraldehyde for 30 minutes at room temperature. Thyroglobulin-conjugated peptide (1.5 ml) was removed and mixed with 3.5 ml water, then aliquoted into 10 sterile vials of 0.5 ml each for immunizations. Antigen (100 μg) plus 500 μl phosphate buffered saline (PBS) was emulsified in 500 μl Freund's complete adjuvant. This preparation was used to immunize rabbits at two week intervals. The rabbits were bled at 5 weeks post-injection and the blood was centrifuged to remove blood cells.

Alternatively, a polyclonal antisera designated anti-A6 was developed after immunization of rabbits with the thrombin-cleaved recombinant A6, expressed as a glutathione-S-transferase-A6 fusion protein. The prokaryotic expression vector pGEX-KG containing the glutathione-S-transferase coding region was provided by Dr. Jack Dixon (Guan and Dixon, (1991) *Anal. Biochem.*, 192:262–267). The oligonucleotides used in the polymerase chain reaction were:
5'     AATAAGTCGACTCCCACCAGACCG-GCATCCAAGCAA 3' (SEQ ID NO: 3)
5'     TAATTGTCGACTTAATCAGTAGTAGCT-TCAGTTTCC 3' (SEQ ID NO: 4)

The A6 coding sequence was excised from the β-gal-A6 construct and cloned into the prokaryotic expression vector pUC18 by well known methods. The A6 coding region was then amplified by the polymerase chain reaction using oligonucleotides corresponding to SEQ ID NOS: 3 and 4, resulting in the generation of a 1067 base pair fragment encoding amino acids 2–350 of the human A6 protein tyrosine kinase. This fragment was then cloned into XhoI-digested pGEX-KG by well known methods to generate pGEX-A6. Competent *E. coli* DH5αF' (Gibco-BRL, Gaithersburg, Md.) were transformed with pGEX-A6. Transformants were grown to an $OD_{600}$=0.8–1.0 and expression of the GST-A6 fusion protein was induced by the addition of 1.0 mM IPTG. After a 3 hour incubation, cells were harvested by centrifugation and resuspended in 10 ml PBST (PBS containing 1% Triton X-100, 2 mM EDTA, 0.1% β-mercaptoethanol (BME) and 1 mM PMSF). Cells were lysed by sonication and clarified be centrifugation. One ml cleared lysate was mixed with 2 ml 50% (v/v) glutathione-agarose beads (Sigma) for 30 min at 4° C. The beads were then washed times with PBST, once with thrombin cleavage buffer (50 mM Tris-HCl, pH 8.0, 150 mM NaCl, 2.5 mM $CaCl_2$, 0.1% BME) and resuspended in the same buffer. The resuspended beads were mixed with 6 μg thrombin (Sigma) for 20 min at room temperature and centrifuged. The supernatant containing the recombinant A6 protein cleaved from GST was collected and used to immunize rabbits as described above.

The resulting sera were aliquoted and stored at −80° C. The specificity of the antibody was assessed by solid phase ELISA, immunoprecipitation and Western blotting, techniques all well known in the art.

EXAMPLE 8

Production of monoclonal antibodies against human A6 kinase

For production of monoclonal antibodies, BALB/c mice were injected at two week intervals subcutaneously with 20 μg of recombinant A6 prepared as in Example 7. Three days prior to cell fusion, mice with the highest serum titer against A6 were injected intravenously with 1 μg recombinant A6. On the day of fusion, the mouse was sacrificed and the spleen removed. Fusion of spleen cells and P3-X83 Ag8.653 myeloma cells was performed with polyethylene glycol according to standard techniques (Brown, (1985) *Tissue Culture Meth.*, 9: 137–140) and hybridomas were selected in hypoxanthine-aminopterin-thymidine (HAT) medium. The resulting hybridomas were aliquoted into 96 well tissue culture plates. After approximately 10 to 14 days, the hybridoma supernatants were screened for reactivity with A6 by ELISA. Positive clones were expanded and assayed for reactivity by Western blot analysis. Hybridomas scoring positive were further cloned twice by limiting dilution using 96 well tissue culture plates. Hybridoma supernatants were screened for reactivity with the A6 kinase by ELISA, immunoprecipitation and Western blot analysis. Clones scoring positive were further cloned by limiting dilution. Monoclonal antibodies were isotyped and the ascites purified by protein A-Sepharose chromatography. The resulting antibodies specific for A6 were designated BF2, FG12, GF9, DA6, FH7, EA12, DB7 and BC3. The hybridoma cell lines producing these antibodies are maintained in permanent collection under the same names in the laboratory of Dr. Steven Tronick, National Institutes of Health, National Cancer Institute, Bethesda, Md. Hybridoma cell lines producing the BF2 and DA6 antibodies have been deposited with the American Type Culture Collection (ATCC).

To determine whether any known tyrosine kinase inhibitors could inhibit the A6 kinase, in vitro kinase assays were performed as described in the following example.

EXAMPLE 9

Inhibition of A6 kinase activity

In vitro kinase assays are performed as in Example 4, but in the presence or absence of several known commercially-available (Gibco-BRL, Gaithersburg, Md.; Calbiochem, San Diego, Calif.) tyrosine kinase inhibitors: lavendustin A, genistein, tyrphostin and herbimycin A. Kinase activity in the presence and absence of these inhibitors is compared to determine which is an inhibitor of kinase activity. In addition, the level of inhibition will be compared to that of other known tyrosine kinases to determine whether the A6 inhibition exhibits much greater specificity than that of the other tyrosine kinases. Other tyrosine kinase inhibitors specific to the A6 kinase are also within the scope of the present invention.

Corresponding A6 kinase genes from other species can be readily isolated as described below.

EXAMPLE 10

Isolation of the A6 kinase gene from nonhuman species

Commercially available cDNA libraries from nonhuman species such as mouse (liver, testis, lung) and fish (Stratagene, La Jolla, Calif.) are screened with a labeled human A6 DNA probe derived from restriction digestion of the full length clone described in Example 1 by techniques well known in the art. The clones are plaque-purified and sequenced using, for example, the Sequenase™ kit (United States Biochemical). Open reading frames are aligned with the A6 sequence using computer programs such as the NCBI BLAST network service searches of NCBI databases to determine whether the isolated clones encode proteins exhibiting significant homology to the human A6 protein tyrosine kinase.

Several additional features of the A6 protein sequence suggest that this enzyme may be involved in pathways regulating cell proliferation. A short stretch of significant similarity to the actin depolymerizing factors (ADF) and the cofilins, proteins known to bind phosphoinositides, was evident (FIG. 1). Over a 30 amino acid region from $phe_{85}$ to $gly_{114}$, A6 was found to be 77%, 42% and 33% related to the ADF from the plants *Lilium longiflorum* and *Acanthamoeba castellanii* and chicken cofilin, respectively. It has been proposed that the corresponding sequence in cofilin (A6 $trp_{88}$ to $met_{99}$) is responsible for binding to actin and phosphoinositides (Yonezawa et al., (1991) *J. Biol. Chem.*, 266: 17218–17221). Thus, A6 may be linked to the control of cytoskeletal organization mediated by actin polymerization and depolymerization. This organization is important for cell growth and differentiation or phosphoinositide turnover, an important cell signalling pathway occurring in response to a variety of external stimuli. Hormones and growth factor binding to cell surface receptors are examples of some types of external stimuli. In addition, the predicted protein sequence of A6 contains a number of consensus phosphorylation sites for several kinases including protein kinase C, casein kinase and tyrosine kinases. These sequence motifs indicate that A6 activity may be regulated by other kinases known to play a central role in cell signalling pathways. The potential N-myristoylation of the A6 kinase suggests that this protein may have oncogenic capabilities and may exert its effects at the cytoplasmic face of the lipid bilayer. If this is the case, inhibitors of A6 kinase activity can be designed and will have potential antiproliferative effects. Lastly, A6 is a ubiquitous protein expressed in many organs and is highly conserved phylogenetically.

There will be various modifications, improvements and applications of the disclosed invention apparent to those of skill in the art, and the present application is intended to cover such embodiments. It is intended, therefore, that the full scope of these embodiments be measured by the following claims.

What is claimed is:

1. An isolated polynucleotide encoding the human A6 protein tyrosine kinase.

2. The polynucleotide of claim 1, wherein said polynucleotide has the sequence corresponding to the coding region of SEQ ID NO: 1.

3. A recombinant construct comprising the coding region of SEQ ID NO: 1 operably linked to a heterologous promoter in an expression vector.

4. Isolated cells transfected with the recombinant construct of claim 3.

5. The cells of claim 4 wherein said cells are prokaryotic.

6. The prokaryotic cells of claim 5, wherein said cells are *E. coli* Y1089 cells.

7. The construct of claim 3, wherein said expression vector is λpCEVlacz, said vector containing the galactosidase promoter and gene sequence.

8. The construct of claim 7 wherein the sequence corresponding to SEQ ID NO: 1 is adjacent to said β-galactosidase gene, wherein upon expression the protein encoded by said SEQ ID NO: 1 and said β-galactosidase form a fusion protein.

9. Isolated human A6 protein tyrosine kinase having a molecular weight of about 40,000 daltons.

10. The protein kinase of claim 9, wherein said kinase has the sequence corresponding to SEQ ID NO: 2.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 3000 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 61..1113

( x i ) SEQUENCE DESCRIPTION: SEQ ID NO:1:

```
CCGCCGGCCG GGGCGCCTGG CTGCACTCAG CGCCGGAGCC GGGAGCTAGC GGCCGCCGCC        60

ATG TCC CAC CAG ACC GGC ATC CAA GCA AGT GAA GAT GTT AAA GAG ATC         108
Met Ser His Gln Thr Gly Ile Gln Ala Ser Glu Asp Val Lys Glu Ile
 1           5                  10                  15

TTT GCC AGA GCC AGA AAT GGA AAG TAC AGA CTT CTG AAA ATA TCT ATT         156
Phe Ala Arg Ala Arg Asn Gly Lys Tyr Arg Leu Leu Lys Ile Ser Ile
             20                  25                  30

GAA AAT GAG CAA CTT GAG ATT GGA TCA TAT AGT CAG CCT TCA GAT TCC         204
Glu Asn Glu Gln Leu Glu Ile Gly Ser Tyr Ser Gln Pro Ser Asp Ser
         35                  40                  45

TGG GAT AAG GAT TAT GAT TCC TTT GTT TTA CCC CTG TTG GAG GAC AAA         252
Trp Asp Lys Asp Tyr Asp Ser Phe Val Leu Pro Leu Leu Glu Asp Lys
     50                  55                  60

CAA CCA TGC TAT ATA TTA TTC AGG TTA GAT TCT CAG AAT GCC CAG GGA         300
Gln Pro Cys Tyr Ile Leu Phe Arg Leu Asp Ser Gln Asn Ala Gln Gly
 65                  70                  75                  80

TAT GAA TGG ATA TTC ATT GCA TGG TCT CCA GAT CAT TCT CAT GTT CGT         348
Tyr Glu Trp Ile Phe Ile Ala Trp Ser Pro Asp His Ser His Val Arg
                 85                  90                  95

CAA AAA ATG TTG TAT GCA GCA ACA AGA GCA ACT CTG AAG AAG GAA TTT         396
Gln Lys Met Leu Tyr Ala Ala Thr Arg Ala Thr Leu Lys Lys Glu Phe
             100                 105                 110

GGA GGT GGC CAC ATT AAA GAT GAA GTA TTT GGA ACA GTA AAG GAA GAT         444
Gly Gly Gly His Ile Lys Asp Glu Val Phe Gly Thr Val Lys Glu Asp
         115                 120                 125

GTA TCA TTA CAT GGA TAT AAA AAA TAC TTG CTG TCA CAA TCT TCC CCT         492
Val Ser Leu His Gly Tyr Lys Lys Tyr Leu Leu Ser Gln Ser Ser Pro
 130                 135                 140

GCC CCA CTG ACT GCA GCT GAG GAA GAA CTA CGA CAG ATT AAA ATC AAT         540
Ala Pro Leu Thr Ala Ala Glu Glu Glu Leu Arg Gln Ile Lys Ile Asn
145                 150                 155                 160

GAG GTA CAG ACT GAC GTG GGT GTG GAC ACT AAG CAT CAA ACA CTA CAA         588
Glu Val Gln Thr Asp Val Gly Val Asp Thr Lys His Gln Thr Leu Gln
                 165                 170                 175

GGA GTA GCA TTT CCC ATT TCT CGA GAA GCC TTT CAG GCT TTG GAA AAA         636
Gly Val Ala Phe Pro Ile Ser Arg Glu Ala Phe Gln Ala Leu Glu Lys
             180                 185                 190

TTG AAT AAT AGA CAG CTC AAC TAT GTG CAG TTG GAA ATA GAT ATA AAA         684
Leu Asn Asn Arg Gln Leu Asn Tyr Val Gln Leu Glu Ile Asp Ile Lys
         195                 200                 205

AAT GAA ATT ATA ATT TTG GCC AAC ACA ACA AAT ACA GAA CTG AAA GAT         732
Asn Glu Ile Ile Ile Leu Ala Asn Thr Thr Asn Thr Glu Leu Lys Asp
 210                 215                 220

TTG CCA AAG AGG ATT CCC AAG GAT TCA GCT CGT TAC CAT TTC TTT CTG         780
Leu Pro Lys Arg Ile Pro Lys Asp Ser Ala Arg Tyr His Phe Phe Leu
225                 230                 235                 240

TAT AAA CAT TCC CAT GAA GGA GAC TAT TTA GAG TCC ATA GTT TTT ATT         828
Tyr Lys His Ser His Glu Gly Asp Tyr Leu Glu Ser Ile Val Phe Ile
                 245                 250                 255

TAT TCA ATG CCT GGA TAC ACA TGC AGT ATA AGA GAG CGG ATG CTG TAT         876
Tyr Ser Met Pro Gly Tyr Thr Cys Ser Ile Arg Glu Arg Met Leu Tyr
             260                 265                 270

TCT AGC TGC AAG AGC CGT CTG CTA GAA ATT GTA GAA AGA CAA CTA CAA         924
Ser Ser Cys Lys Ser Arg Leu Leu Glu Ile Val Glu Arg Gln Leu Gln
         275                 280                 285

ATG GAT GTA ATT AGA AAG ATC GAG ATA GAC AAT GGG GAT GAG TTG ACT         972
Met Asp Val Ile Arg Lys Ile Glu Ile Asp Asn Gly Asp Glu Leu Thr
 290                 295                 300

GCA GAC TTC CTT TAT GAA GAA GTA CAT CCC AAG CAG CAT GCA CAC AAG        1020
```

| Ala | Asp | Phe | Leu | Tyr | Glu | Glu | Val | His | Pro | Lys | Gln | His | Ala | His | Lys | |
|-----|-----|-----|-----|-----|-----|-----|-----|-----|-----|-----|-----|-----|-----|-----|-----|---|
| 305 | | | | | 310 | | | | 315 | | | | | | 320 | |

| CAA | AGT | TTT | GCA | AAA | CCA | AAA | GGT | CCT | GCA | GGA | AAA | AGA | GGA | ATT | CGA | 1068 |
|-----|-----|-----|-----|-----|-----|-----|-----|-----|-----|-----|-----|-----|-----|-----|-----|------|
| Gln | Ser | Phe | Ala | Lys | Pro | Lys | Gly | Pro | Ala | Gly | Lys | Arg | Gly | Ile | Arg | |
| | | | | 325 | | | | | 330 | | | | | 335 | | |

| AGA | CTA | ATT | AGG | GGC | CCA | GCG | GAA | ACT | GAA | GCT | ACT | ACT | GAT | TAAAGTCATC | 1120 |
|-----|-----|-----|-----|-----|-----|-----|-----|-----|-----|-----|-----|-----|-----|------------|------|
| Arg | Leu | Ile | Arg | Gly | Pro | Ala | Glu | Thr | Glu | Ala | Thr | Thr | Asp | | |
| | | | | 340 | | | | 345 | | | | | 350 | | |

```
ACATTAAACA  TTGTAATACT  AGTTTTTTAA  AAGTCCAGCT  TTTAGTACAG  GAGAACTGAA    1180
ATCATTCCAT  GTTGATATAA  AGTAGGGAAA  AAATTTGTAC  TTTTTGGAAA  ATAGCACTTT    1240
TCACTTCTGT  GTGTTTTTAA  AATTAATGTT  ATAGAAGACT  CATGATTTCT  ATTTTTGAGT    1300
TAAAGCTAGA  AAAGGGTTCA  ACATAATGTT  TAATTTTGTC  ACACTGTTTT  CATAGCGTTG    1360
ATTCCACACT  TCAAATACTT  CTTAAAATTT  TATACAGTTG  GGCCAGTTCT  AGAAAGTCTG    1420
ATGTCTCAAA  GGGTAAACTT  ACTACTTTCT  TGTGGGACAG  AAAGACCTTA  AAATATTCAT    1480
ATTACTTAAT  GAATATGTTA  AGGACCAGGC  TAGAGTATTT  TCTAAGCTGG  AAACTTAGTG    1540
TGCCTTGGAA  AAGCCGCAAG  TTGCTTACTC  CGAGTAGCTG  TGCTAGCTCT  GTCAGACTGT    1600
AGGATCATGT  CTGCAACTTT  TAGAAATAGT  GCTTTATATT  GCAGCAGTCT  TTTATATTTG    1660
ACTTTTTTTT  AATAGCATTA  AAATTGCAGA  TCAGCTCACT  CTGAAACTTT  AAGGGTACCA    1720
GATATTTCT   ATACTGCAGG  ATTTCTGATG  ACATTGAAAG  ACTTTAAACA  GCCTTAGTAA    1780
ATTATCTTTC  TAATGCTCTG  TGAGGCCAAA  CATTTATGTT  CAGATTGAAA  TTTAAATTAA    1840
TATCATTCAA  AAGGAAACAA  AAAATGTTGA  GTTTTAAAAA  ATCAGGATTG  ACTTTTTTCT    1900
CAAAACCATA  CATTTATGGG  CAAATTGTGT  TCTTTATCAC  TTCCGAGCAA  ATACTCAGAT    1960
TTAAAATTAC  TTTAAAGTCC  TGGTACTTAA  CAGGCTAACG  TAGATAAACA  CCTTAATAAT    2020
CTCAGTTAAT  ACTGTATTTC  AAAACACATT  TAACTGTTTT  CTAATGCTTT  GCATTATCAG    2080
TTACAACCTA  GAGAGATTTT  GAGCCTCATA  TTTCTTTGAT  ACTTGAAATA  GAGGGAGCTA    2140
GAACACTTAA  TGTTTAATCT  GTTAAACCTG  CTGCAAGAGC  CATAACTTTG  AGGCATTTTC    2200
TAAATGAACT  GTGGGGATCC  AGGATTTGTA  ATTTCTTGAT  CTAAACTTTA  TGCTGCATAA    2260
ATCACTTATC  GGAAATGCAC  ATTTCATAGT  GTGAAGCACT  CATTTCTAAA  CCTTATTATC    2320
TAAGGTAATA  TATGCACCTT  TCAGAAATTT  GTGTTCGAGT  AAGTAAAGCA  TATTAGAATA    2380
ATTGTGGGTT  GACAGATTTT  TAAAATAGAA  TTTAGAGTAT  TTGGTGTTTT  GTTTGTTTAC    2440
AAATAATCAG  ACTATAATAT  TTAAACATGC  AAAATAACTG  ACAATAATGT  TGCACTTGTT    2500
TACTAAAGAT  ATAAGTTGTT  CCATGGGTGG  ACACGTAGAC  AGACACACAT  ACACCCAAAT    2560
TATTGCATTA  AGAATCCTGG  AGCAGACCAT  AGCTGAAGCT  GTTATTTCA   GTCAGGAAGA    2620
CTACCTGTCA  TGAAGGTATA  AAATAATTTA  GAAGTGAATG  TTTTTCTGTA  CCATCTATGT    2680
GCAATTATAC  TCTAAATTCC  ACTACACTAC  ATTAAAGTAA  ATGGACATTC  CAGAATATAG    2740
ATGTGATTAT  AGTCTTAAAC  TAATTATTAT  TAAACCAATG  ATTGCTGAAA  ATCAGTGATG    2800
CATTTGTTAT  AGAGTATAAC  TCATCGTTTA  CAGTATGTTT  TAGTTGGCAG  TATCATACCT    2860
AGATGGTGAA  TAACATATTC  CCAGTAAATT  TATATAGCAG  GGAAGAATTA  CATGCCTTCT    2920
GGTGGACATT  TTATAAGTGC  ATTTATATC   ACAATAAAAA  TTTTTTCTCT  TTAAAAAAAA    2980
AAACAAGAAA  AAAAAAAAA                                                    3000
```

( 2 ) INFORMATION FOR SEQ ID NO:2:

( i ) SEQUENCE CHARACTERISTICS:
        ( A ) LENGTH: 350 amino acids ( B ) TYPE: amino acid
( D ) TOPOLOGY: linear ( i i ) MOLECULE TYPE: protein ( x i ) SEQUENCE DESCRIPTION: SEQ ID NO:2:

| Met | Ser | His | Gln | Thr | Gly | Ile | Gln | Ala | Ser | Glu | Asp | Val | Lys | Glu | Ile |
| 1 | | | | 5 | | | | | 10 | | | | | 15 | |

| Phe | Ala | Arg | Ala | Arg | Asn | Gly | Lys | Tyr | Arg | Leu | Leu | Lys | Ile | Ser | Ile |
| | | | 20 | | | | | 25 | | | | | 30 | | |

| Glu | Asn | Glu | Gln | Leu | Glu | Ile | Gly | Ser | Tyr | Ser | Gln | Pro | Ser | Asp | Ser |
| | | 35 | | | | | 40 | | | | | 45 | | | |

| Trp | Asp | Lys | Asp | Tyr | Asp | Ser | Phe | Val | Leu | Pro | Leu | Leu | Glu | Asp | Lys |
| | 50 | | | | | 55 | | | | | 60 | | | | |

| Gln | Pro | Cys | Tyr | Ile | Leu | Phe | Arg | Leu | Asp | Ser | Gln | Asn | Ala | Gln | Gly |
| 65 | | | | | 70 | | | | | 75 | | | | | 80 |

| Tyr | Glu | Trp | Ile | Phe | Ile | Ala | Trp | Ser | Pro | Asp | His | Ser | His | Val | Arg |
| | | | | 85 | | | | | 90 | | | | | 95 | |

| Gln | Lys | Met | Leu | Tyr | Ala | Ala | Thr | Arg | Ala | Thr | Leu | Lys | Lys | Glu | Phe |
| | | | 100 | | | | | 105 | | | | | 110 | | |

| Gly | Gly | Gly | His | Ile | Lys | Asp | Glu | Val | Phe | Gly | Thr | Val | Lys | Glu | Asp |
| | | 115 | | | | | 120 | | | | | 125 | | | |

| Val | Ser | Leu | His | Gly | Tyr | Lys | Lys | Tyr | Leu | Leu | Ser | Gln | Ser | Ser | Pro |
| | 130 | | | | | 135 | | | | | 140 | | | | |

| Ala | Pro | Leu | Thr | Ala | Ala | Glu | Glu | Glu | Leu | Arg | Gln | Ile | Lys | Ile | Asn |
| 145 | | | | | 150 | | | | | 155 | | | | | 160 |

| Glu | Val | Gln | Thr | Asp | Val | Gly | Val | Asp | Thr | Lys | His | Gln | Thr | Leu | Gln |
| | | | | 165 | | | | | 170 | | | | | 175 | |

| Gly | Val | Ala | Phe | Pro | Ile | Ser | Arg | Glu | Ala | Phe | Gln | Ala | Leu | Glu | Lys |
| | | | | 180 | | | | | 185 | | | | | 190 | |

| Leu | Asn | Asn | Arg | Gln | Leu | Asn | Tyr | Val | Gln | Leu | Glu | Ile | Asp | Ile | Lys |
| | | | 195 | | | | | 200 | | | | | 205 | | |

| Asn | Glu | Ile | Ile | Ile | Leu | Ala | Asn | Thr | Thr | Asn | Thr | Glu | Leu | Lys | Asp |
| | 210 | | | | | 215 | | | | | 220 | | | | |

| Leu | Pro | Lys | Arg | Ile | Pro | Lys | Asp | Ser | Ala | Arg | Tyr | His | Phe | Phe | Leu |
| 225 | | | | | 230 | | | | | 235 | | | | | 240 |

| Tyr | Lys | His | Ser | His | Glu | Gly | Asp | Tyr | Leu | Glu | Ser | Ile | Val | Phe | Ile |
| | | | | 245 | | | | | 250 | | | | | 255 | |

| Tyr | Ser | Met | Pro | Gly | Tyr | Thr | Cys | Ser | Ile | Arg | Glu | Arg | Met | Leu | Tyr |
| | | | 260 | | | | | 265 | | | | | 270 | | |

| Ser | Ser | Cys | Lys | Ser | Arg | Leu | Leu | Glu | Ile | Val | Glu | Arg | Gln | Leu | Gln |
| | | 275 | | | | | 280 | | | | | 285 | | | |

| Met | Asp | Val | Ile | Arg | Lys | Ile | Glu | Ile | Asp | Asn | Gly | Asp | Glu | Leu | Thr |
| | 290 | | | | | 295 | | | | | 300 | | | | |

| Ala | Asp | Phe | Leu | Tyr | Glu | Glu | Val | His | Pro | Lys | Gln | His | Ala | His | Lys |
| 305 | | | | | 310 | | | | | 315 | | | | | 320 |

| Gln | Ser | Phe | Ala | Lys | Pro | Lys | Gly | Pro | Ala | Gly | Lys | Arg | Gly | Ile | Arg |
| | | | | 325 | | | | | 330 | | | | | 335 | |

| Arg | Leu | Ile | Arg | Gly | Pro | Ala | Glu | Thr | Glu | Ala | Thr | Thr | Asp |
| | | | 340 | | | | | 345 | | | | | 350 |

( 2 ) INFORMATION FOR SEQ ID NO:3:

( i ) SEQUENCE CHARACTERISTICS:
( A ) LENGTH: 36 base pairs
( B ) TYPE: nucleic acid
( C ) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

AATAAGTCGA CTCCCACCAG ACCGGCATCC AAGCAA                36

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

TAATTGTCGA CTTAATCAGT AGTAGCTTCA GTTTCC                36

(2) INFORMATION FOR SEQ ID NO:5:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:5:

Phe Ile Phe Trp Ala Pro Glu Ser Ala Pro Leu Lys Ser Lys Met Ile
1               5                   10                  15

Tyr Ala Ser Ser Lys Asp Ala Ile Lys Lys Lys Phe Thr Gly
            20                  25                  30

(2) INFORMATION FOR SEQ ID NO:6:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:6:

Phe Ile Leu Trp Ala Pro Asp Ser Ala Pro Ile Lys Ser Lys Met -Met
1               5                   10                  15

Tyr Thr Ser Thr Lys Asp Ser Ile Lys Lys Lys Leu Val Gly
            20                  25                  30

(2) INFORMATION FOR SEQ ID NO:7:

(i) SEQUENCE CHARACTERISTICS:
    (A) LENGTH: 30 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:7:

Phe Ile Ser Trp Ser Pro Asp Thr Ser Arg Val Arg Ser Lys Met Leu
1               5                   10                  15

Tyr Ala Ser Thr Lys Asp Arg Phe Lys Arg Glu Leu Asp Gly
            20                  25                  30

(2) INFORMATION FOR SEQ ID NO:8:

(i) SEQUENCE CHARACTERISTICS:
    (A) LENGTH: 19 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:8:

Gly Phe Asp Arg Lys His Pro Phe Tyr Trp Xaa Xaa Ser Thr Ala Gly
1               5                   10                  15

Cys Asn Pro